United States Patent [19]
Sih

[11] Patent Number: 5,912,349
[45] Date of Patent: Jun. 15, 1999

[54] PROCESS FOR THE PREPARATION OF ROQUINIMEX

[75] Inventor: John C. Sih, Kalamazoo, Mich.

[73] Assignee: Pharmacia & Upjohn Company, Kalamazoo, Mich.

[21] Appl. No.: 09/006,097

[22] Filed: Jan. 13, 1998

Related U.S. Application Data

[60] Provisional application No. 60/036,032, Jan. 31, 1997.
[51] Int. Cl.$^6$ .................................................. C07D 215/22
[52] U.S. Cl. ............................................... 546/155
[58] Field of Search ............................................... 546/155

[56] References Cited

U.S. PATENT DOCUMENTS 4,738,971  4/1988  Eriksoo et al. ........................ 514/312

*Primary Examiner*—Patricia L. Morris
*Attorney, Agent, or Firm*—Bruce Stein

[57] ABSTRACT

The present invention is an improved process to prepare roquinimex (IV)

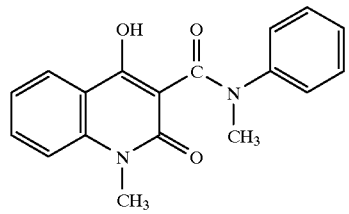

which comprises:

(1) contacting N-methyl-N-phenyl-α-carbomethoxyamide (V) with from about one to about two equivalents of base and (2) contacting the mixture of step (1) with N-methylisatoic anhydride (I).

6 Claims, No Drawings

PROCESS FOR THE PREPARATION OF ROQUINIMEX

CROSS-REFERENCE TO RELATED APPLICATIONS

This application claims the benefit of US provisional application Ser. No. 60/036,032 filed Jan. 31, 1997, under 35 USC §119(e)(i).

BACKGROUND OF THE INVENTION

1. Field of the Invention

The present invention is an improved process to produce roquinimex.

2. Description of the Related Art

U.S. Pat. No. 4,738,971 discloses roquinimex and a method to produce it. The disclosed method starts with N-methylisatoic anhydride (I) and requires three steps. The improved process of the present invention starts with the same N-methylisatoic anhydride (I) and requires fewer steps.

SUMMARY OF INVENTION

Disclosed is a process to prepare roquinimex (IV) which comprises:

(1) contacting N-methyl-N-phenyl-α-carbomethoxyamide (V) with from about one to about two equivalents of base and (2) contacting the mixture of step (1) with N-methylisatoic anhydride (I).

DETAILED DESCRIPTION OF THE INVENTION

Roquinimex (IV) is known, see U.S. Pat. No. 4,738,971. Further, U.S. Pat. No. 4,738,971 discloses a three step process to make roquinimex (IV). In the three step process, the starting N-methylisatoic anhydride (I) is converted to the corresponding ester (II). The ester (II) is then hydrolyzed with acid to the corresponding acid (III) which is then reacted with the appropriate secondary amine, φ—NH—$CH_3$, to form the expected amide, roquinimex (IV).

The improved process of the present invention is a greatly simplified process. The diketo compound (V), N-methyl-N-phenyl-α-carbomethoxyamide, $CH_3$—O—CO—$CH_2$—CO—N($CH_3$)(φ), which is preferably produced by the process of EXAMPLE 1, is contacted with a base to form an anion. The anion produced is then reacted directly with N-methylisatoic anhydride (I) to form roquinimex (IV).

It is preferable to use N-methyl-N-phenyl-α-carbomethoxyacetamide (V, EXAMPLE 1) however N-methyl-N-phenyl-α-carboethoxyacetamide is also operable and will produce the desired roquinimex.

About one to about two equivalents of base are operable. With much less than one eqivalent or significantly more than two the reaction does not produce satisfactory yields. It is preferred that the base be present in an amount of about one equivalent.

Suitable bases included $C_1$–$C_4$ alkoxides such as methoxide, ethoxide, propioxide and butoxide. Preferred bases include sodium or potassium butoxide.

The process of the present invention is practiced according to EXAMPLE 2. It is preferred to perform the claimed process in an aprotic solvent. Suitable aprotic solvents include DMF, THF, glyme, dioxane and ether and mixtures thereof.

The roquinimex produced by the process of the invention (EXAMPLE 2) can be upgraded or purified by the process of EXAMPLE 3.

Roquinimex is known to be useful as a pharmaceutical agent, see U.S. Pat. No. 4,738,971. It is preferably used in treating multiple sclerosis, in particular the treatment of relapsing remitting and secondary progressive multiple sclerosis. In treating multiple sclerosis roquinimex is administered in an oral dose of from about 2.0 to about 5.0 mg/day.

DEFINITIONS AND CONVENTIONS

The definitions and explanations below are for the terms as used throughout this entire document including both the specification and the claims.

DEFINITIONS

All temperatures are in degrees Centigrade.

TLC refers to thin-layer chromatography.

HPLC refers to high pressure liquid chromatography.

THF refers to tetrahydrofuran.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

UV refers to ultraviolet spectroscopy.

–φ refers to phenyl ($C_6H_5$).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

NNNNNN-NN-N refers to Chemical Abstracts Service (CAS, Columbus, Ohio) registry numbers where each "N" is an integer from 0 thru 9, but deleting leading zeros in the 6-digit portion of the number. Registry numbers are assigned to a particular chemical compound by CAS criteria, provided that the compound has been found to exist and it has been characterized in some way. Compounds published from approximately 1967 to the present are registered publicly and the registry number is the key to finding references in the CAS data base for such a registered compound. The CAS data base is publicly available from several database vendors such as STN International, System Development Corporation (SDC) Orbit Search Service, Lockheed Dialog, Bibliographic Retrieval Systems, Questrel, etc. CAS registry numbers are included in the EXAMPLES for some of the compounds which have been registered.

N-Methylisatoic anhydride refers to the compound of formula (I).

Roquinimex refers to N-phenyl-N-methyl-1,2-dihydro-4-hydroxy-1-methyl-2-oxoquinoline-3-carboxamide the compound of formula (IV), also known as LINOMIDE.

N-Methyl-N-phenyl-α-carbomethoxyamide refers to $CH_3$—O—CO—$CH_2$—CO—N($CH_3$)(φ) (V) which as a CAS number of 84088-88-0.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

N-Methyl-N-Phenyl-α-Carbomethoxyacetamide (V)

Mono-methyl malonate potassium salt also known as potassium methyl malonate (73.32 g, 0.47 mol) and water (50 ml) are cooled to 5° with an ice bath, and concentrated hydrochloric acid (40 ml) is added over a 30 minute period while the temperature is maintained below 10°. The mixture is filtered with suction to remove potassium chloride, and the precipitate washed with methyl t-butylether (75 ml). The aqueous layer of the filtrate is separated and washed with methyl t-butyl ether (3×50 ml). The combined methyl t-butyl ether extracts are dried over anhydrous sodium sulfate; then the solvent was removed under reduced pressure at 45–50° to give carbomethoxy acetic acid. This product was checked by NMR for complete removal of the methyl t-butyl ether solvent.

Carbomethoxy acetic acid (100 g, 0.84 mol) is dissolved in methylene chloride (400 ml). Thionyl chloride (100 g, 0.84 mol) is added via a dropping funnel. It can be added rapidly as there is little, if any, exotherm produced during the addition. After addition, the reaction is refluxed at 40–45° for 1 hr. At the end of the reflux period, 50% of the methylene chloride is removed (200 ml) by distillation at atmospheric pressure and 40–45°. Fresh methylene chloride is added (200 ml) followed by distillation to again remove 50% of the total volume. This add-distillation procedure is repeated two times to give the carbomethoxy acetyl chloride.

The carbomethoxy acetyl chloride mixture is cooled in an ice-salt bath to −5 to 0° and N-methyl aniline (55.64 g, 0.52 mol) in methylene chloride (200 ml) is added at a rate so as to maintain the temperature of the reaction mixture between −5 to 0°. The addition is performed using an addition funnel and can normally be carried out over a 3–5 min time period to control the slight exotherm. Pyridine (66.36 g, 0.84 mol) in methylene chloryde (200 ml) is then added to the above mixture. The addition rate is adjusted so as to keep the temperature of the reaction between −5 to 0° during the addition. The addition is performed using an addition funnel and can normally be carried out over a 3–5 min time period to control the slight exotherm. After the addition is complete (as measured by HPLC) the reaction is quenched by pouring the reaction mixture into water (500 ml) and stirring continued for 30 min. The reaction is equilibrated and the methylene chloride layer separated. Additional methylene chloride (400–500 ml) is added and the methylene chloride mixture is washed successively with hydrochloric acid (1N, 2×300 ml), saturated sodium bicarbonate solution (2×300 ml), saline (1×600 ml) and the methylene chloride mixture dried through anhydrous sodium sulfate. Concentration of the mixture under reduced pressure at 40–45° gives the title compound, HPLC (Nucleosil column; acetonitrile/water, 45/55, 1 ml/min, UV=229 nm; Retention times for N-methyl-N-phenyl-α-carbomethoxyacetamide~6.0 min; N-methyl aniline~11.0–12.0 min.

Example 2

Preparation of Roquinimex (IV) from N-Methylisotoic anhydride (I) and N-Methyl-α-carbomethoxyacetamide (V)

N-Methyl-N-phenyl-α-carbomethoxyacetamide (V, EXAMPLE 1, 139 g, 0.671 mole) and DMF (695 mL). The mixture is subject to reduced pressure and purged with nitrogen three times. While at room temperature (20–25°), potassium t-butoxide solution (1.714 M in THF, 367 mL, 0.630 mole) is added in one portion. A small exotherm and slight darkening of the mixture followed this addition. The mixture is heated to 80–90° and kept at this temperature for 1.5 hr.

A −78° cooling bath is placed on the receiving flask of the distillation assembly, the nitrogen flow is shut off and the mixture is subject to reduced pressure over 0.5 hr to remove the THF solvent. The pot temperature at the end of the distillation is 72–76°. The amount of distillate collected should be nearly identical to the amount of potassium tert-butoxide reagent used, (367 ml). The mixture is then heated to 80–85° and N-methylisotoic anhydride (I, 70.72 g, 0.400 mole) is added in one portion followed by a 5–10 mL DMF wash. Gas evolution with foaming followed the addition and subsequent wash. The equipment is modified at this point to include a reflux condenser with a vacuum port. With the temperature still at 80–85°, the mixture is placed under reduced pressure and the mixture refluxed for 30 min. After refluxing the temperature is 79°. The reduced pressure and heat source are removed, the system is repressurized with nitrogen and the temperature is allowed to drop to 30° (±2°). Hydrochloric acid (0.6 N, 2.295 L) is added slowly via an addition funnel attached to the claisen head over 2.5 hr, to pH=1.0–1.5, making sure the temperature does not exceed 32°. The temperature control is especially critical at the beginning of the addition when a mild exotherm occurs. The temperature at the end of the addition is nearly room temperature (24–25°). When the acid addition is complete, the resulting slurry is stirred for 30 min and then let stand overnight before filtration. The solids are washed with water (2 ×330 mL) and dried on a nitrogen press to give the title compound, HPLC (Nucleosil column; acetonitrile/water, 45/55, 1 ml/min, UV=229 nm; Retention times 2.29 min.

Example 3

Purification of Roquinimex (IV)

Roquinimex crude is taken up in water (1.5 L) and the slurry is stirred vigorously at 20–25°. The pH is adjusted to 7.5–7.7 with sodium hydroxyde (7%, about 170 mL). (The base can be added as fast as possible but requires longer pH equilibration near the end of the addition (about 1–2 hr total addition time). It is recommended that 85% of the base is initially added to a stable pH and the rest is added dropwise until the pH has stabilized and falls into the desired range of 7.5–7.7.) Nearly all solids should be dissolved (some may remain however). After the base is added and the pH is stabilized for more than 30 min, Darco (charcoal, 15.00 g) is added and the mixture is stirred for 30 min. The mixture is filtered through a 0.45 micron Millipore filter and the filter cake is washed with water (2×175 mL). The filtrate is transferred to a flask.

The mixture is stirred vigorously, heated to 28–32° and hydrochloric acid (6 N, about 120 mL) is added over 30 to 45 min to a pH of 0.5 to 1.0. After the addition is over, the mixture is stirred for 15 min then allowed to stand, without stirring, at the above temperature for 2 hr before filtration. The filter cake is washed with water (2×180 mL) and dried on a nitrogen press to give essentially pure title compound.

CHART A

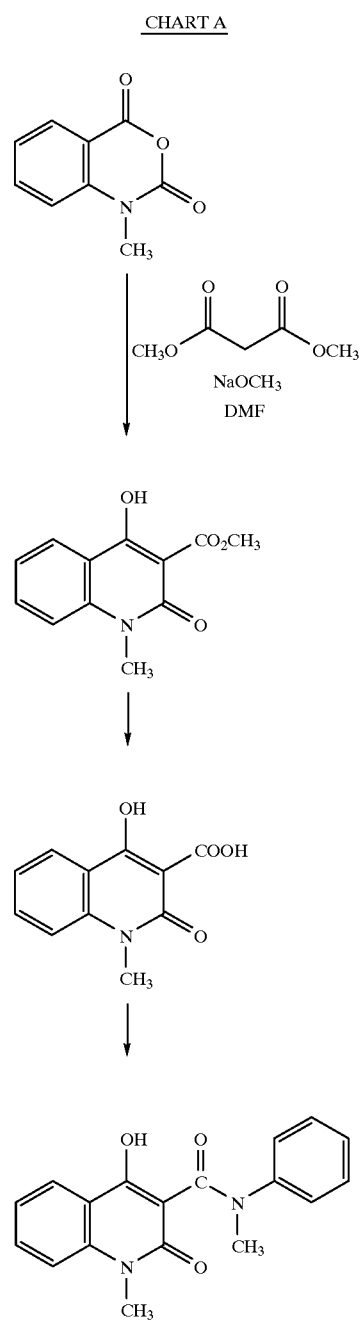

CHART B (I)

[structure: N-methylisatoic anhydride]

+

(V)

[structure: CH₃O-C(O)-CH₂-C(O)-NCH₃Ph]

↓

(IV)

[structure: roquinimex]

I claim:

1. A process to prepare roquinimex (IV) which comprises:

(1) contacting N-methyl-N-phenyl-α-carbomethoxyamide (V) with from about one to about two equivalents of base and (2) contacting the mixture of step (1) with N-methylisatoic anhydride (I).

2. A process according to claim 1 where the base is present in an amount of about one equivalent.

3. A process according to claim 1 where the base is selected from the group consisting of alkoxides where the alkyl portion is $C_1$–$C_4$ alkyl.

4. A process according to claim 3 where the base is sodium or potassium butoxide.

5. A process according to claim 1 where the process is performed in the presence of an aprotic solvent.

6. A process according to claim 5 where the aprotic solvent is selected from the group consisting of DMF, THF, glyme, dioxane and ether and mixtures thereof.

* * * * *